United States Patent [19]

Hibert

[11] Patent Number: 5,109,006
[45] Date of Patent: Apr. 28, 1992

[54] CERTAIN PHARMACEUTICALLY ACTIVE 6H-IMIDAZO[1,2-A]PYRIDINE-5-ONES

[75] Inventor: Marcel Hibert, Eschau, France

[73] Assignee: Merrell Dow Pharmaceuticals Inc., Cincinnati, Ohio

[21] Appl. No.: 750,758

[22] Filed: Aug. 22, 1991

Related U.S. Application Data

[63] Continuation of Ser. No. 637,082, Jan. 3, 1991, abandoned, which is a continuation-in-part of Ser. No. 452,925, Dec. 18, 1989, abandoned.

[30] Foreign Application Priority Data

Dec. 20, 1988 [EP] European Pat. Off. ........ 88403255.8

[51] Int. Cl.$^5$ .............. A61K 31/44; C07D 471/04
[52] U.S. Cl. .................... 514/278; 514/224.2; 514/224.5; 514/229.8; 514/230.5; 514/249; 514/250; 514/300; 544/6; 544/32; 544/52; 544/70; 544/101; 544/105; 544/230; 544/344; 544/353; 546/18; 546/121
[58] Field of Search .............. 514/224.2, 224.5, 229.8, 514/230.5, 249, 250, 278, 300; 544/6, 32, 52, 70, 101, 105, 230, 344, 353; 546/18, 121

[56] References Cited

U.S. PATENT DOCUMENTS 4,044,015 8/1977 Kuhla ..................... 546/121
4,612,312 9/1986 Hibert et al. ............ 514/278

FOREIGN PATENT DOCUMENTS 0120589 10/1984 European Pat. Off.
949226 2/1949 France.
2322597 4/1977 France.

OTHER PUBLICATIONS

James R. Piper et al., Journal of Medicinal Chemistry, vol. 14, No. 4, pp. 350–354 (1981).

*Primary Examiner*—Bernard Dentz
*Attorney, Agent, or Firm*—Carolyn D. Moon

[57] ABSTRACT

This invention relates to novel derivatives of 1,7'-[imidazo-[1,2-a]pyridine]5'-(6'H)ones, to the method for their preparation and to their use as anti-hypertensive, anxiety, anti-depressant and anti-migraine agents, and to their use as appetite regulators useful for the treatment of anorexia and obesity.

21 Claims, No Drawings

CERTAIN PHARMACEUTICALLY ACTIVE 6H-IMIDAZO[1,2-A]PYRIDINE-5-ONES

CROSS-REFERENCE TO RELATED APPLICATIONS

This is a continuation of application Ser. No. 07/637,082 filed Jan. 3, 1991, now abandoned which is a continuation-in-part of application Ser. No. 07/452,925 having a filing date of Dec. 18, 1989, now abandoned.

This invention relates to novel derivatives of 1,7'-[imidazo-[1,2-a]pyridine]5'-(6'H)ones, to the method for their preparation and to their use as anti-anxiety, antidepressant and anti-migraine agents, and to their use as appetite stimulants useful for the treatment of anorexia.

More specifically, this invention relates to 1,7'-[imidazo-[1,2-a]pyridine]5'-(6'H)ones of the formula

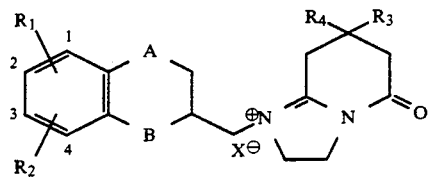

their enantiomers and tautomers, wherein each of A and B represents oxygen, sulfur or $NR_5$ with $R_5$ being H or $C_{1-4}$ alkyl, $R_1$ is H, $C_{1-4}$ alkyl, $C_{1-4}$ alkoxy, halogeno, nitro, OH, $SO_3H$, or $SO_2NH_2$, $R_2$ is H, $C_{1-4}$ alkyl, $C_{1-4}$ alkoxy, halogeno or hydroxy, and $R_1$, $R_2$ taken together with the carbon atoms to which they are attached form a fused benzenoid moiety at the 1,2 or 3,4 positions, each of $R_3$ and $R_4$ are methyl or when taken together with the carbon atom to which they are attached form a cyclopentane or cyclohexane moiety, and $X^\ominus$ represents an anion forming a pharmaceutically acceptable salt with the cation with which it is associated.

As used herein the term "a 1 to 4 carbon alkyl group" is taken to mean a straight or branched alkyl group of from 1 to 4 carbon atoms. Illustrative examples of a 1 to 4 carbon alkyl group as used herein are methyl, ethyl, n-propyl, isopropyl, n-butyl and isobutyl. Similarly, the term "a 1 to 4 carbon alkoxy group" is taken to mean a straight or branched alkoxy group of from 1 to 4 carbon atoms. Illustrative examples of a 1 to 4 carbon alkoxy group as used herein are methoxy, ethoxy, n-propoxy, isopropoxy, n-butoxy, and isobutoxy. The term "halogen group" is taken to mean a fluorine, chlorine or bromine atom.

The term "pharmaceutically acceptable acid addition salts" embraces those salts capable of being formed by the interaction of an organic or inorganic acid with a pharmaceutical base compound to yield a non-toxic pharmaceutically acceptable entity, such as that illustrated by compounds of Formula IV. Illustrative inorganic acids which form suitable salts include hydrochloric, hydrobromic, sulphuric and phosphoric acid and acid metal salts such as sodium monohydrogen orthophosphate and potassium hydrogen sulfate. Illustrative organic acids which form suitable salts include the mono-, di- and tricarboxylic acids. Illustrative of such acids are, for example, acetic, glycolic, lactic, pyruvic, malonic, succinic, glutaric, fumaric, malic, tartaric, citric, ascorbic, maleic, hydroxymaleic, benzoic, hydroxybenzoic, phenylacetic, cinnamic, salicylic, 2-phenoxybenzoic and sulfonic acids such as methane sulfonic acid and 2-hydroxyethane sulfonic acid. Either the mono- or the di-acid salts can be formed, and such salts can exist in either a hydrated or a substantially anhydrous form. In general, salts of these compounds are crystalline materials which are soluble in water and various hydrophilic organic solvents.

Preferred compounds of this invention are those compounds of Formula I wherein A and B are oxo and wherein $R_3$ and $R_4$ represent methyl groups or when taken together with the carbon atom to which they are attached form a cyclopentane ring. Another preferred group are those compounds wherein $R_1$ and $R_2$ are hydrogen or wherein one or both of $R_1$ and $R_2$ are methoxy.

Another preferred group of compounds are those compounds of Formula I wherein one of A and B is oxo and the other is an imino group wherein $R_6$ is hydrogen or a $C_{1-4}$ alkyl.

Yet another preferred group of compounds are those wherein $R_1$ and $R_2$, when taken together with the carbon atoms to which they are attached, form a benzenoid moiety at the 1,2 or 3,4-positions (said positions being as designated in Formula I) and A and B are oxo.

Specifically preferred compounds of Formula I are those compounds of the following chart:

| $R_1$ | $R_2$ | A | B | $R_3$ | $R_4$ |
|---|---|---|---|---|---|
| H | H | O | O | $CH_3$ | $CH_3$ |
| H | H | O | O | cyclopentane | |
| 1-$OCH_3$* | H | O | O | $CH_3$ | $CH_3$ |
| 1-$OCH_3$ | H | O | O | cyclopentane | |
| 4-$OCH_3$ | H | O | O | $CH_3$ | $CH_3$ |
| 4-$OCH_3$ | H | O | O | cyclopentane | |
| H | H | O | NH | $CH_3$ | $CH_3$ |
| H | H | NH | O | $CH_3$ | $CH_3$ |

*(wherein the position of the methoxy group is as indicated on the benzenoid moiety of the structure of Formulae I and IV.)

The most preferred compound is 2',3',7',8'-tetrahydro-1'-[(2,3-dihydro-1,4-benzodioxin-2-yl)-methyl]-spirocyclopentane-1,7'-imidazo[1,2-a]-pyridin]-5'-(6'H)-one, methanesulfonate, hydrate.

The compounds of Formula I may readily be prepared by heating the appropriate glutarimide derivatives (Formula IV), in the form of their pharmaceutically acceptable acid addition salt, at temperatures of about 150° C. to 200° C. under an inert atmosphere, using argon or nitrogen, for about 2 to 10 hours. The resulting compounds, in the form of their acid addition salts, are formed as a vitreous residue which are crushed to afford solid amorphous materials. The so-prepared products must be stored under an inert atmosphere. Of course, the heating of the glutarimide derivatives (IV) may be effected in a solvent but this presents isolation problems.

The glutarimide derivatives (IV) are prepared by standard techniques using processes analogously known by those in the art, preferably by the condensation of an appropriate heterocyclomethylamino nucleophile of Formula II with a glutarimide of Formula III according to the process outlined in Reaction Scheme A.

Reaction Scheme A

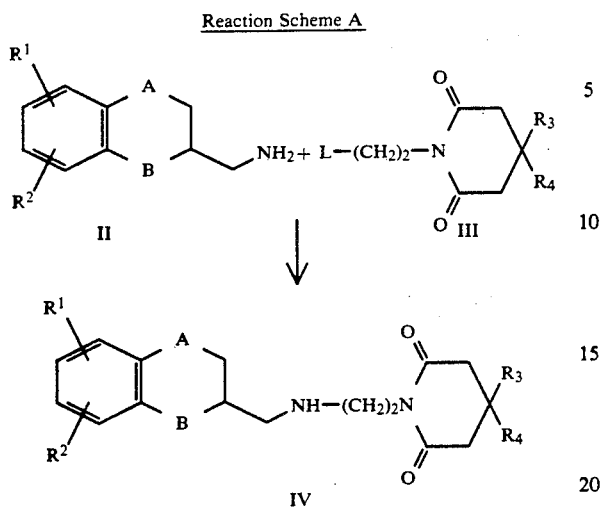

wherein $R_1$, $R_2$, $R_3$, $R_4$, A and B are as defined above in Formula I and L represents a suitable leaving group.

The nucleophilic condensation reaction is preferably performed by allowing approximately equimolar amounts of the nucleophile (II) and the substrate (III) to react from about 1 hour to about 24 hours, depending upon the reactants, the solvent and the temperature at which the reaction is conducted. The reaction temperature can range from 25° C. to about 150° C., preferably from about 60° C. to about 150° C.

Inasmuch as the reactants employed are typically crystalline solids, the use of solvents in this reaction is preferred. Suitable solvents include any non-reactive solvent, preferably those having a boiling point in the range of from 60° C. to 150° C., as for example, petroleum ether; chlorinated hydrocarbons such as carbon tetrachloride, ethylene chloride, methylene chloride or chloroform; chlorinated aromatics such as 1,2,4-trichlorobenzene, or o-dichlorobenzene; carbon disulfide; an ethereal solvent such as diethylether, tetrahydrofuran or p-dioxane; an aromatic solvent such as benzene, toluene or xylene; or an alcoholic solvent such as ethanol. Especially preferred solvents are those known to promote nucleophilic reactions such as dimethylsulfoxide and dimethylformamide.

The products of the reaction (IV) can be isolated by any appropriate techniques, such as filtering to remove any solid materials and subsequently evaporating the solvent from the filtrate and purifying, by standard techniques known to the art, such as, for example, using their picric or oxalic acid complexes.

The glutarimide reactants (II) may be prepared by standard techniques well known in the art. In general such reactants may be prepared according to Reaction Scheme B, wherein A, B, $R_1$ and $R_2$ are as previously defined.

Reaction Scheme B

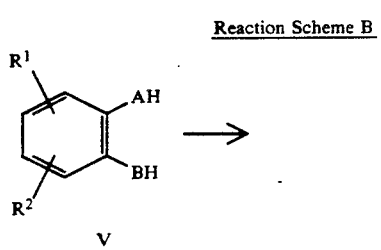

-continued
Reaction Scheme B

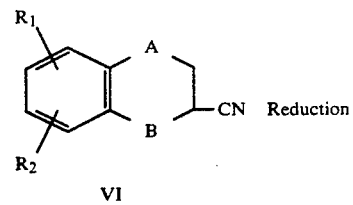

In essence the compounds of Formula V are reacted with a 2-chloro or 2-bromoacrylonitrile, using about equimolar quantities of the reactants, in the presence of about 2 or more equivalents of a base (e.g. potassium carbonate) in a suitable solvent at temperatures of about 0° C. to about the reflux temperature of the reaction mixture, generally for a period of about 1 to 24 hours.

Suitable solvents include dimethylformamide; dimethylsulfoxide; acetone; chlorinated hydrocarbons such as carbon tetrachloride, chloroform or methylene chloride; ethereal solvents such as diethylether, tetrahydrofuran or diglyme; aromatic solvents such as benzene, toluene or xylene; or alcoholic solvents such as methanol or ethanol.

Where A and B represent different atoms, or where $R_1$ and $R_2$ are different, a mixture of products will be obtained. These mixtures can be readily separated and purified by methods commonly known to those skilled in the art, such as by chromatography on silica gel or fractional recrystallization. Furthermore, when the $R_1$ or $R_2$ groups of a Structure V compound are a hydroxy group, this hydroxy group must be protected prior to undergoing the above-described condensation reaction with 2-bromo- or 2-chloroacrylonitrile. Suitable protecting groups include benzyl or methyl groups and the removal of the protecting group can be accomplished by any suitable means generally known to the art, such as by catalytic reduction of the benzyl group or by treatment with an acid such as hydrobromic acid or boron tribromide.

The reduction of the cyano derivatives (VI) can be accomplished with a number of reagent systems including catalytic reductions employing hydrogen gas and a catalytic metal such as palladium on charcoal, Raney nickel, platinum, rhodium, ruthenium or platinum oxide; diborane; sodium borohydride; dissolving metal reductions utilizing lithium, sodium, potassium, calcium, zinc, magnesium, tin or iron in liquid ammonia or a low-molecular weight aliphatic amine or sodium, aluminum or zinc amalgam, zinc, tin or iron in a hydroxylic solvent or in the presence of an aqueous mineral acid; or lithium aluminum hydride.

Preferably, the cyano derivatives (VI) are reduced using one to 2 molar equivalents, preferably about 1.5 molar equivalents, of lithium aluminum hydride in a suitable solvent. The reaction is allowed to proceed from about 30 minutes to about 24 hours, preferably from about 1 to 5 hours, depending upon the reactants, the solvent and temperature. Suitable temperatures are from −78° C. to 60° C., preferably about 20° C. Suitable solvents include ethereal solvents such as diethyl ether, tetrahydrofuran, p-dioxane, 1,2-dimethoxyethane, diglyme or an aromatic solvent such as benzene, toluene or xylene.

The reactants of Formula III may readily be prepared using standard procedures well known in the art, such as that outlined in Reaction Scheme C.

Reaction Scheme C

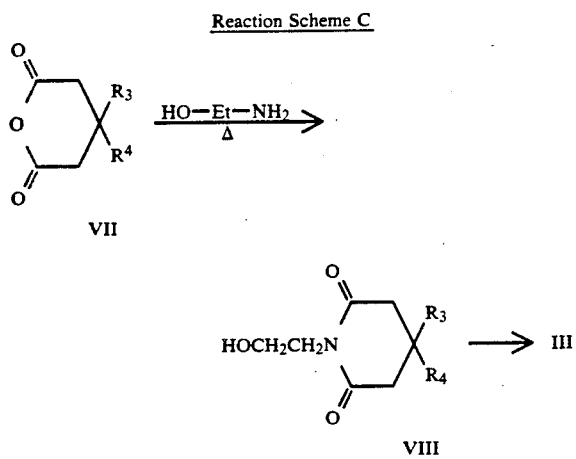

wherein $R_3$ and $R_4$ are as previously defined, and Et is a bridging ethylene moiety.

The alcohols of Formula VIII may be prepared using known amidation procedures such as by reacting approximately equimolar quantities of hydroxyethyl amine with a glutaric anhydride (VII) (although in practice, it is preferred to use a slight excess of one or the other reactant). Preferably the reaction is effected by refluxing the reactants together in an inert solvent such as benzene or toluene. The reaction is allowed to proceed at the reflux temperature of the mixture for about 12 to 24 hours taking care to continously remove any water formed during the reaction such as by means of a Dean-Stark apparatus or such other means to azeotropically remove in situ-formed water.

The leaving groups of compounds (III) can be any group known to those skilled in the art, as for example an ester of a sulfuric or sulfonic acid [e.g. a tosylate (OTS) or mesylate (OMS)], an iodide, bromide or chloride or a hydroxyl group. Compounds bearing a tosylate are preferred and such compounds may be prepared by treating the corresponding alcohol VIII with a base such as potassium carbonate and subsequently adding a slight molar excess of tosyl chloride. The reaction temperature ranges from $-78°$ C. to about 60° C. and preferably from 0° C. to room temperature. The reaction is allowed to proceed for about 1 hour to about 12 hours depending on the reactants, the temperature and the solvent. Suitable solvents include dimethylformamide; dimethylsulfoxide; acetone; aromatic solvents such as benzene, toluene or xylene; or an ethereal solvent such as diethyl ether, tetrahydrofuran or 1,2-dimethoxyethane. A hydrogen halide acceptor is preferably employed to react with the hydrogen halide that forms during the reaction. For this purpose, one or more molar equivalents of an organic nitrogen base can be employed. Suitable organic nitrogen bases include tri(-lower alkyl)amines such as triethylamine, or an aromatic amine such as pyridine, a picoline or a collidine. Pyridine and the picolines and collidines can be utilized in a large excess, serving also as the reaction solvent. Of course, compounds bearing the other leaving groups can also be prepared by methods well known in the art. The following specific examples further illustrate the preparation of compounds embraced in the instant invention.

EXAMPLE 1

2-Cyanobenzodioxan[1,4]

Pyrocatechol (12 g, 0.11 mol), potassium carbonate (41.1 g, 0.3 mol) and 2-chloroacrylonitrile (8 ml, 0.1 mol) are mixed in acetone (200 ml) and boiled at the reflux for 18 hours under a nitrogen atmosphere. The mixture is cooled, the solid filtered off and the solvent evaporated under reduced pressure. The oily residue is dissolved in methylene chloride, washed with water, potassium hydroxide (5%) and hydrochlorid acid (5%). The organic solution is dried over sodium sulphate and concentrated. The residual oil (15.73 g) is then distilled (120° C., 0.05 mmHg) to give a colorless oil (13.25 g) which then crystallizes to the title compound (yield: 83%), m.p. 54° C.

EXAMPLE 2

2-Aminomethyl-benzodioxan[1,4]

2-Cyanobenzodioxan[1,4] (13.2 g, 82 mM) dissolved in dry tetrahydrofuran (150 ml) is added dropwise at 0° C., under nitrogen atmosphere, to $LiALH_4$ (4.91 g, 122 mM) suspended in dry tetrahydrofuran (100 ml). The mixture is warmed to reflux for 1.5 hours, then cooled in an ice bath. Hydrolysis is performed by adding dropwise a saturated solution of NH4Cl. Dry sodium sulfate is added and solids are filtered off to afford, after evaporation of the solvent, a yellow oil (10.1 g). The hydrochloride is made using HCl gas in dry $Et_2O$. The solid title compound obtained is recrystallized in a MeOH-/AcOEt mixture (yield: 60%), m.p.: 220° C.

EXAMPLE 3

N-(4-Hydroxyethyl)-3,3-tetramethylene glutarimide

4-Hydroxyethylamine (30 ml, 318.9 mM) is added to a solution of 3,3-tetramethylene glutaric anhydride (56.35 g, 335 mM) in dry toluene (650 ml). The mixture is heated to reflux with a Dean-Stark apparatus during 20 hours. The mixture is cooled, the solvent evaporated and the residue dissolved in ethyl acetate. This organic phase is washed with HCl (5%), NaOH (5%), brine and dried over sodium sulfate. The solvent is evaporated under reduced pressure affording the title compound as a sticky yellow oil (68.1 g). Flash chromatography with a 5:3 mixture of ethyl acetate and methylene chloride as eluent allows for the obtention of the title compound.

EXAMPLE 4

N-(4-Tosyloxyethyl)-3,3-tetramethylene glutarimide

N-(4-Hydroxyethyl)-3,3-tetramethylene glutarimide (179.6 mM) is dissolved in pyridine (600 ml). Potassium carbonate (50 g) is added. The mixture is cooled to 0° C. in an ice bath and tosyl chloride (197.5 ml) is slowly added under an inert atmosphere. The reaction mixture is stirred during 1 hour at 0° C. and 4.5 hours at room temperature. The end of the reaction is checked by thin layer chromatography. Inorganic salts are filtered off, pyridine is evaporated under vacuum and the oily residue is dissolved in methylene chloride, washed with water, aqueous sodium carbonate and water again. Drying over sodium sulfate and evaporation of the solvent affords a crude oil. Flash chromatography on silica gel yields the title compound.

EXAMPLE 5

2,3-Dihydronaphtho[1,2b]dioxin-2 and 3-ylnitrile

The compound 1,2-dihydroxynaphthalene (2 g, 11.2 mM), 2-chloro acrylonitrile (0.95 ml) and potassium carbonate (4.9 g, 35.4 mM) are mixed in 40 ml of dry acetone under argon, and refluxed for 18 hours. The solid residue is filtered, and the filtrate evaporated to dryness. The reddish oil residue is dissolved in ethyl acetate and this solution is washed successively with water, dilute potassium hydroxide, hydrochloric acid solution sand brine, dried over sodium sulphate and evaporated to dryness. The remaining oil so obtained (2.17 g) is purified by flash chromatography (silica, toluene/hexane 2/1) to yield 1.58 g (67%) of a white solid, which is a mixture of the two possible isomers.

EXAMPLE 6

2- and 3-(Aminomethyl)-2,3-dihydronaphtho[1,2,b]dioxin

The mixture of 2,3-dihydronaphtho[1,2b]dioxin-2 and 3-ylnitrile, as obtained in the preceding example, is dissolved in 30 ml of dry tetrahydrofuran. This solution is slowly added to a suspension of LiAlH4 (0.45 g, 11.2 mM) contained in 5 ml of dry tetrahydrofuran, at 0° C., under an atmosphere of argon. The mixture is stirred for 3 hours at room temperature, hydrolyzed with a saturated solution of ammonium chloride, diluted with methylene chloride, filtered and dried over anhydrous sodium sulfate.

The oil which is obtained following evaporation (1.61 g) is repetitively flash chromatographed on silica (CH2Cl2, MeOH 9/1) to produce the two almost pure separated isomers.

EXAMPLE 7

8-[2-(1,4-Benzodioxan-2-ylmethylamino)ethyl]-8-azaspiro[4,5]decane-7,9-dione The compound 2-aminomethyl-benzodioxane[1,4] in its methanesulfonate form (1 equivalent) is dissolved in dry dimethylformamide. An excess of potassium carbonate is added thereto. N-(2-tosyloxyethyl)-3,3-tetramethylene glutarimide (1 equivalent), dissolved in dry dimethylformamide (25 ml), is slowly added with stirring under an inert atmosphere. The mixture is stirred overnight at 120° C.; the solid is filtered; and the dimethylformamide is removed by distillation under reduced pressure. The oily residue is dissolved in ethyl acetate, washed with H2O and extracted with HCl (5%). The acid extract is made alkaline with potassium carbonate and extracted with ethyl acetate. The resulting organic extract is washed with brine, dried over sodium sulfate and the solvent is removed under vacuum to yield a yellow oil. This crude material is purified by flash chromatography on silica gel (AcOEt), leading to the pure title compound. The hydrochloride salt is formed in isopropanol with 1 equivalent of concentrated hydrochloric acid. Recrystallization in isopropanol provides white crystals, m.p. 177° C.

Following essentially the same procedure, but substituting the compound 2-aminomethyl-benzoxazine[1,4] for the 2-aminomethyl-benzodioxane[1,4] above, the compound 8-[4-(1,4-benzoxazine-2-ylmethylamino)ethyl]-8-azaspiro[4,5]-decane-7,9-dione may be obtained.

EXAMPLE 8

(−)8-[4-(1,4-Benzodioxan-2-ylmethylamino)ethyl]-8-azaspiro[4,5]decane-7,9-dione 8-[2-(1,4-Benzodioxan-2-ylmethylamino)ethyl]-8-azaspiro[4,5]decane-7,9-dione (0.91 g) is dissolved in a mixture of acetone and isopropanol. (+) Binaphthyl phosphoric acid (BNP) (0.82 g), dissolved in acetone, is added to the previous solution, leading to the formation of the white crystals, which are removed by filtration, washed with i-PrOH, EtOH and acetone.

The resulting residue is suspended in water and basified with potassium carbonate. The free base so obtained is extracted with ethyl acetate. The organic extract is dried and evaporated affording the crude optically enriched free base. The remaining traces of BNP, K+ salt are removed by rapid filtration over silica (AcOEt/MeOH=97/3) yielding the pure free base (0.44 g).

The hydrochloride salt is formed in Et2O and recrystallized in EtOH for the expected product.

By following essentially the same procedure but substituting (−)bynaphthyl phosphoric acid (BNP) for (+)BNP, the remaining enantiomer (+)8-[4-(1,4-benzodioxan-2-ylmethylamino)ethyl]-8-azaspiro[4,5]-decane-7,9-dione, HCl salt, may be obtained.

EXAMPLE 9

8-[4-(2,3-Dihydro-naphtho[1,2,b]dioxin-2-ylmethylamino)ethyl]-8-azaspiro[4,5]decane-7,9-dione 2,3-Dihydro-2-methylamino naphtho(1,2,b)dioxin iodide, (1.096 g, 3.1 mM), an equivalent amount of N-(4-tosyloxyethyl)-3,3-tetramethylene glutarimide produced as in Example IV (Formula III R3,R4=cyclopentyl) and an excess of potassium carbonate are mixed in 30 ml of dry dimethylformamide under an argon atmosphere. After warming 17 hours at 100° C., the mixture is filtered, dimethylformamide is evaporated, the residual oil dissolved in AcOEt, washed with water and extracted in diluted hydrochloric acid. The resulting solution is made alkaline and extracted with AcOEt. The organic phase is dried on sodium sulfate and evaporated to provide 1.53 g of a crude oil.

Purification by flash chromatography on silica (MeOH/CH2Cl2 5/95) affords 0.62 g of the pure product. The hydrochloride is recrystallized in AcOH/CH2Cl2/i-PrOH, m.p. 228° C.

Following essentially the same procedure but substituting 2,3-dihydro-3-methyl-amino-methylnaphtho[1,2,b]dioxin for the isomer of the same mixture, one obtains the other pure isomer.

EXAMPLE 10

2',3',7',8'-tetrahydro-1'-[(2,3-dihydro-1,4-benzodioxin-2-yl)methyl]spirocyclopentane-1,7'-imidazo[1,2-a]-pyridin]-5'-(6'H)-one, methanesulfonate, hydrate A 0.5 g portion of the compound of Example 7 (in its methanesulfonate form) in a round bottom flask equipped with a serum cap and a continuous flow of argon is heated to about 190° C. for 2 hours at which time all of the compound has been transformed into a vitreous residue. The residue is crushed to afford pure 2',3',7',8'-tetrahydro-1'-[(2,3-dihydro-1,4-benzodioxin-2-yl)methyl]spirocyclopentane-1,7'-imidazo[1,2-a]pyridin]-5'-(6'H)-one, methanesulfonate, hydrate as white crystals, m.p. 80° C. (N.B. Handle and store under an inert atmosphere).

The structure I compounds are useful therapeutic agents possessing antianxiety, antidepressant, antimigraine and antihypertensive properties and are capable of exerting beneficial effects on appetite in the treatment of anorexia and obesity. The compounds of this invention can be administered either orally, parenterally such as subcutaneously, intravenously, intramuscularly or intraperitoneally or rectally. The preferred route of administration of the compounds of this invention is orally. The quantity of novel compound administered will vary depending on the patient, the mode of administration and severity of the anxiety or hypertension to be treated and can be any effective amount. Repetitive daily administration of the compounds may be desired and will vary with the patient's condition and the mode of administration.

For oral administration, the antianxiety effective amount of a Structure I compound is from 0.005 to 10 mg/kg of patient body weight per day, preferably from 0.05 to 5 mg/kg of patient body weight per day. The preferred antianxiety dose of the Structure I compound wherein $R_1$ and $R_2$ are hydrogen atoms, A and B are oxygen atoms, and $R_4$ and $R_5$ together with the carbon atom to which they are attached form a cyclopentane ring is about 0.1 mg/kg of patient body weight per day. Pharmaceutical compositions in unit dose form can contain from 1 to 50 mg of active ingredient and can be taken one or more times per day in divided doses to achieve the prescribed daily dosage.

For parenteral administration, an antianxiety effective amount of a Structure I compound is from about 0.005 to 10 mg/kg of patient body weight per day, preferably from about 0.05 to 5 mg/kg of patient body weight per day. A parenteral composition in unit dose form can contain from 0.1 mg to 10 mg of active ingredient and can be taken one or more times per day in divided doses to achieve the prescribed daily dosage.

As used herein with respect to the treatment of migraine, depression, anxiety symptoms, the term patient is taken to mean a human. As used herein with respect to the treatment of hypertension, anorexia or obesity, the term patient is taken to mean warm blooded animals, for example birds, such as chickens and turkeys, in addition to mammals, such as primates, humans, sheep, horses, bovines, pigs, dogs, cats, rats and mice.

For oral administration the compounds can be formulated into solid or liquid preparations such as capsules, pills, tablets, lozenges, melts, powders, solutions, suspensions or emulsions. The solid unit dosage forms are those generally employed such as capsules or tablets. Capsules can be of the ordinary gelatin type containing additional excipients such as surfactants, lubricants and inert fillers such as lactose, sucrose, and cornstarch. In another embodiment the compounds of Structure I can be tableted with conventional tablet bases such as lactose, sucrose, and cornstarch in combination with binders, such as acacia, cornstarch or gelatin, disintegrating agents such as potato starch or alginic acid, and lubricants such as stearic acid or magnesium stearate.

For parenteral administration the compounds may be administered as injectable dosages of a solution or suspension of the compound in a physiologically acceptable diluent with a pharmaceutical carrier. Suitable diluents or carriers include sterile liquids such as water or oils, with or without the addition of surfactants or other pharmaceutically acceptable adjuvants. Illustrative of various oils which can be employed in the practice of this invention are those of petroleum, animal, vegetable, or synthetic origin, for example, peanut oil, soybean oil, and mineral oil. In general, water, saline, aqueous dextrose and related sugar solutions, ethanol and glycols such as propylene glycol or polyethylene glycol are preferred liquid carriers, particularly for injectable solutions.

We claim:

1. A compound of the formula

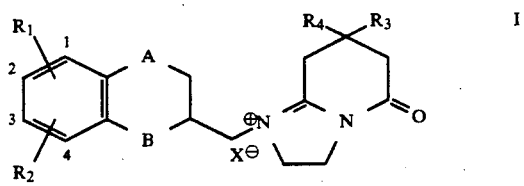

their enantiomers and tautomers, wherein
each of A and B represents oxygen, sulfur or $NR_5$ with $R_5$ being H or $C_{1-4}$ alkyl,
$R_1$ is H, $C_{1-4}$ alkyl, $C_{1-4}$ alkoxy, halogeno, nitro, OH, $SO_3H$, or $SO_2NH_2$,
$R_2$ is H, $C_{1-4}$ alkyl, $C_{1-4}$ alkoxy, halogeno or hydroxy, and $R_1$, $R_2$ taken together with the carbon atoms to which they are attached form a fused benzenoid moiety at the 1,2 or 3,4 positions, each of $R_3$ and $R_4$ are methyl or when taken together with the carbon atom to which they are attached form a cyclopentane or cyclohexane moiety, and $X^\ominus$ represents an anion forming a pharmaceutically acceptable salt with the cation with which it is associated.

2. A compound of claim 1 wherein A and B are oxygen.

3. A compound of claim 1 wherein one of A or B is oxygen and the other is nitrogen.

4. A compound of claim 1 wherein each of $R_3$ and $R_4$ are methyl.

5. A compound of claim 1 wherein each of $R_3$ and $R_4$, together with the carbon atom to which they are attached form a cyclopentane moiety.

6. A compound of claim 1 wherein one of $R_1$ and $R_2$ is methoxy.

7. A compound of claim 1 wherein each of $R_1$ and $R_2$ are hydrogen.

8. A compound of claim 1 wherein $R_1$ and $R_2$ are hydrogen, A and B are oxygen, and $R_3$ and $R_4$ are methyl.

9. A compound of claim 1 wherein $R_1$ and $R_2$ are methyl, A and B are oxygen, and $R_3$ and $R_4$ form a spirocyclopentane moiety.

10. A compound of claim 1, said compound being 2',3',7',8'-tetrahydro-1'-[(2,3-dihydro-1,4-benzodioxin-2-yl)methyl]spirocyclopentane-1,7'-imidazo[1,2-a]-pyridin]-5'-(6'H)-one, methanesulfonate, hydrate.

11. A process for preparing a compound of the formula

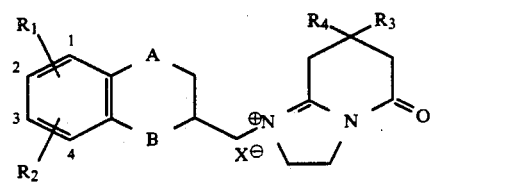

their enantiomers and tautomers, wherein
each of A and B represents oxygen, sulfur or NR$_5$ with R$_5$ being H or C$_{1-4}$ alkyl,
R$_1$ is H, C$_{1-4}$ alkyl, C$_{1-4}$ alkoxy, halogeno, nitro, OH, SO$_3$H, or SO$_2$NH$_2$,
R$_2$ is H, C$_{1-4}$ alkyl, C$_{1-4}$ alkoxy, halogeno or hydroxy, and R$_1$, R$_2$ taken together with the carbon atoms to which they are attached form a fused benzenoid moiety at the 1,2 or 3,4 positions, each of R$_3$ and R$_4$ are methyl or when taken together with the carbon atom to which they are attached form a cyclopentane or cyclohexane moiety, and X$^\ominus$ represents an anion forming a pharmaceutically acceptable salt with the cation with which it is associated, which comprises heating a compound of the formula

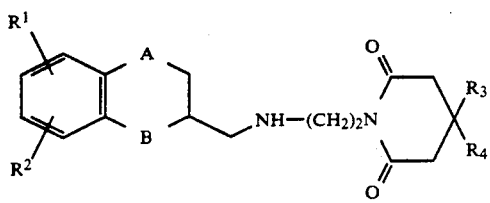

IV in the form of their pharmaceutically acceptable salts thereof, until a vitreous residue is formed.

12. A pharmaceutical composition comprising the compound of claim 1 and a pharmaceutically acceptable carrier.

13. The composition of claim 12 wherein the compound is 2′,3′,7′,8′-tetrahydro-1′-[(2,3-dihydro-1,4-benzodioxin-2-yl)methyl]spirocyclopentane-1,7′-imidazo[1,2-a]-pyridin]-5′-(6′H)-one, methanesulfonate, hydrate.

14. A method for treating anxiety in a patient in need of such therapy comprising administering a therapeutically effective amount of the compound of claim 1.

15. The method of claim 14 wherein the compound is 2′,3′,7′,8′-tetrahydro-1′-[(2,3-dihydro-1,4-benzodioxin-2-yl)methyl]spirocyclopentane-1,7′-imidazo[1,2-a]-pyridin]-5′-(6′H)-one, methanesulfonate, hydrate.

16. A method for treating depression in a patient in need of such therapy comprising administering a therapeutically effective amount of the compound of claim 1.

17. The method of claim 16 wherein the compound is 2′,3′,7′,8′-tetrahydro-1′-[(2,3-dihydro-1,4-benzodioxin-2-yl)methyl]spirocyclopentane-1,7′-imidazo[1,2-a]-pyridin]-5′-(6′H)-one, methanesulfonate, hydrate.

18. A method for treating migraine in a patient in need of such therapy comprising administering a therapeutically effective amount of the compound of claim 1.

19. The method of claim 18 wherein the compound is 2′,3′,7′,8′-tetrahydro-1′-[(2,3-dihydro-1,4-benzodioxin-2-yl)methyl]spirocyclopentane-1,7′-imidazo[1,2-a]-pyridin]-5′-(6′H)-one, methanesulfonate, hydrate.

20. A method for treating anorexia in a patient in need of such therapy comprising administering a therapeutically effective amount of the compound of claim 1.

21. The method of claim 20 wherein the compound is 2′,3′,7′,8′-tetrahydro-1′-[(2,3-dihydro-1,4-benzodioxin-2-yl)methyl]spirocyclopentane-1,7′-imidazo[1,2-a]-pyridin]-5′-(6′H)-one, methanesulfonate, hydrate.

* * * * *